(12) United States Patent
Lu (10) Patent No.: US 7,824,381 B2
(45) Date of Patent: Nov. 2, 2010

(54) SAFETY DISPOSABLE SYRINGE

(75) Inventor: Wen-Chin Lu, Taipei (TW)

(73) Assignees: Lien-Tsang Lee, Taipei (TW); Chih-Hao Lu, Taipei (TW)

( * ) Notice: Subject to any disclaimer, the term of this patent is extended or adjusted under 35 U.S.C. 154(b) by 0 days.

(21) Appl. No.: 11/941,172

(22) Filed: Nov. 16, 2007

(65) Prior Publication Data

US 2009/0131879 A1 May 21, 2009

(51) Int. Cl.
*A61M 5/00* (2006.01)
*A61M 5/32* (2006.01)
(52) U.S. Cl. .................. 604/240; 604/110; 604/195
(58) Field of Classification Search ............. 604/110, 604/187, 192–198, 240, 263
See application file for complete search history.

(56) References Cited

U.S. PATENT DOCUMENTS

| 5,533,975 | A | 7/1996 | Lu |
| 2005/0203458 | A1 * | 9/2005 | Shih ................. 604/110 |
| 2007/0179442 | A1 * | 8/2007 | Shue et al. .......... 604/110 |

FOREIGN PATENT DOCUMENTS

| EP | 0 442 260 A1 | 1/1991 |
| EP | 1 260 242 A1 | 2/2001 |

OTHER PUBLICATIONS

European Search Report for European Application No. 08253734.1: Mar. 16, 2009.

* cited by examiner

*Primary Examiner*—Kevin C Sirmons
*Assistant Examiner*—Imani Hayman
(74) *Attorney, Agent, or Firm*—Stephen A. Bent; Foley & Lardner LLP (57) ABSTRACT

A safety disposable syringe includes: a barrel; a plunger extending into the barrel; a piston mounted on the plunger and formed with a first engaging member; and a needle seat extending fittingly into the barrel and having a front end disposed outwardly of the barrel, and a rear end disposed in the barrel and having a rear end face facing toward the piston. The needle seat defines a fluid passage extending through the rear end face of the rear end of the needle seat. The needle seat is formed with a second engaging member. The fluid passage has a terminating end terminated at the rear end face of the rear end of the needle seat. The second engaging member has a terminating end terminated at the rear end face of the rear end of the needle seat and spaced apart from the first terminating end of the fluid passage.

5 Claims, 12 Drawing Sheets

SAFETY DISPOSABLE SYRINGE

BACKGROUND OF THE INVENTION

1. Field of the Invention

This invention relates to a safety disposable syringe, more particularly to a safety disposable syringe including a barrel and a needle seat provided with a canula and engageable with a piston on a plunger for withdrawing the canula into the barrel prior to disposal of the syringe.

2. Description of the Related Art

Figure 1:
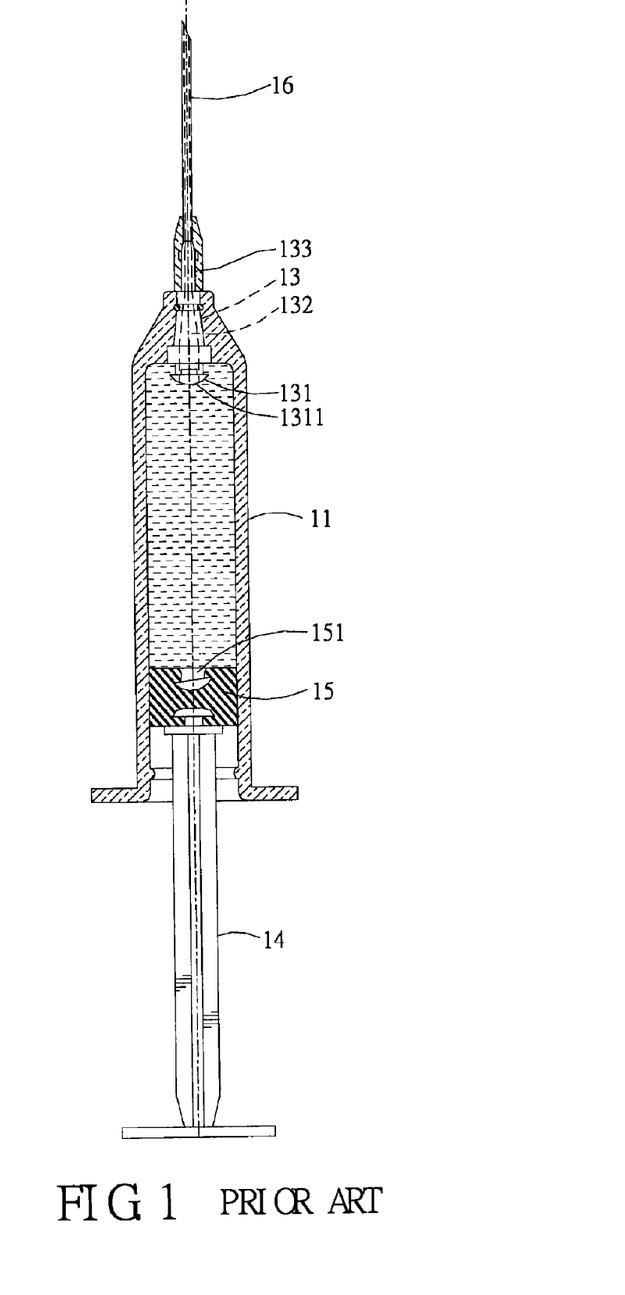
FIG. 1 is a partly sectional view of a conventional safety disposable syringe.

FIG. 1 illustrates a conventional safety disposable syringe that includes a barrel 11, a plunger 14 extending into the barrel 11, a piston 15 mounted on the plunger 14 and formed with an engaging groove 151, and a needle seat 13 extending into the barrel 11, connected to a canula 16, and formed with an engaging tongue 131 that is engageable with the engaging groove 151 so as to permit withdrawal of the canula 16 into the barrel 11 prior to disposal of the safety disposable syringe. The needle seat 13 is formed with a needle channel 133 for extension of the canula 16 thereinto, and a fluid passage 132 extending from one end of the needle channel 133 through an end face 1311 of the engaging tongue 131 so as to permit fluid communication between the canula 16 and a chamber of the barrel 11. However, since the fluid passage 132 passes through the engaging tongue 131, the latter requires a larger size to allow formation of the fluid passage 132 therethrough. As such, the design of the aforesaid safety disposable syringe is not suitable for application to small sized syringes, i.e., syringes that are less than 1 cc in size.

SUMMARY OF THE INVENTION

Therefore, the object of the present invention is to provide a safety disposable syringe that can overcome the aforesaid drawback associated with the prior art.

According to this invention, a safety disposable syringe comprises: a barrel having front and rear open ends and defining a chamber therein and an axis; a plunger extending through the rear open end and into the chamber and having a front end; a piston mounted on the front end of the plunger and formed with a first engaging member; a canula; and a needle seat extending fittingly through the front open end of the barrel and having a front end disposed outwardly of the chamber, and a rear end disposed in the chamber and having a rear end face facing toward the piston. The needle seat defines a central channel extending through the front end of the needle seat for extension of the canula thereinto, and a fluid passage extending through the rear end face of the rear end of the needle seat and in fluid communication with the central channel and the chamber. The rear end face of the rear end of the needle seat is formed with a second engaging member that is axially aligned and that is engagable with the first engaging member. The fluid passage has a first terminating end terminated at the rear end face of the rear end of the needle seat. The second engaging member has a terminating end terminated at the rear end face of the rear end of the needle seat and spaced apart from the first terminating end of the fluid passage.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Before the present invention is described in greater detail, it should be noted that same reference numerals have been used to denote like elements throughout the specification.

Figure 2:
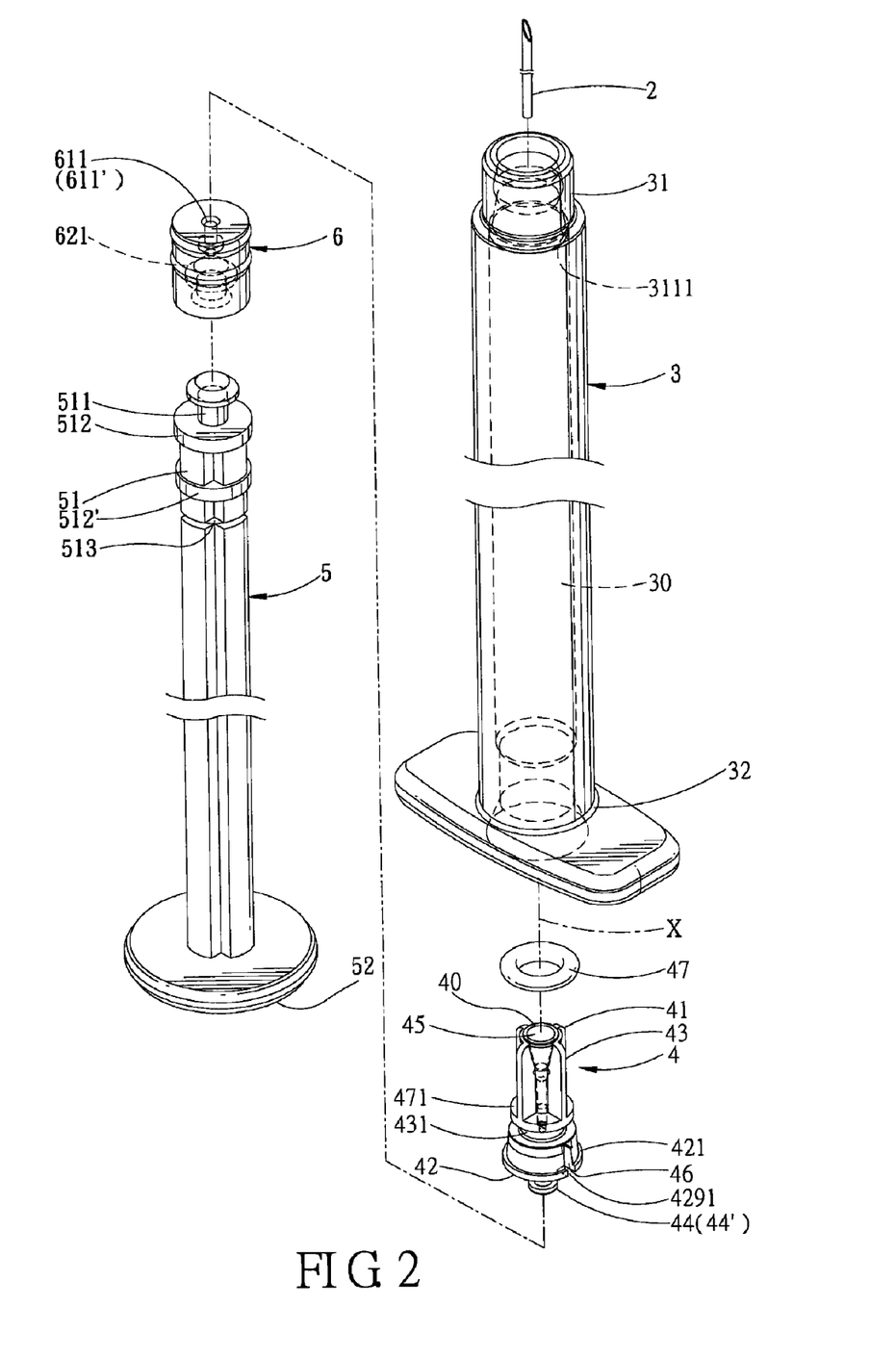
FIG. 2 is an exploded perspective view of the first preferred embodiment of a safety disposable syringe according to this invention.
Figure 3:
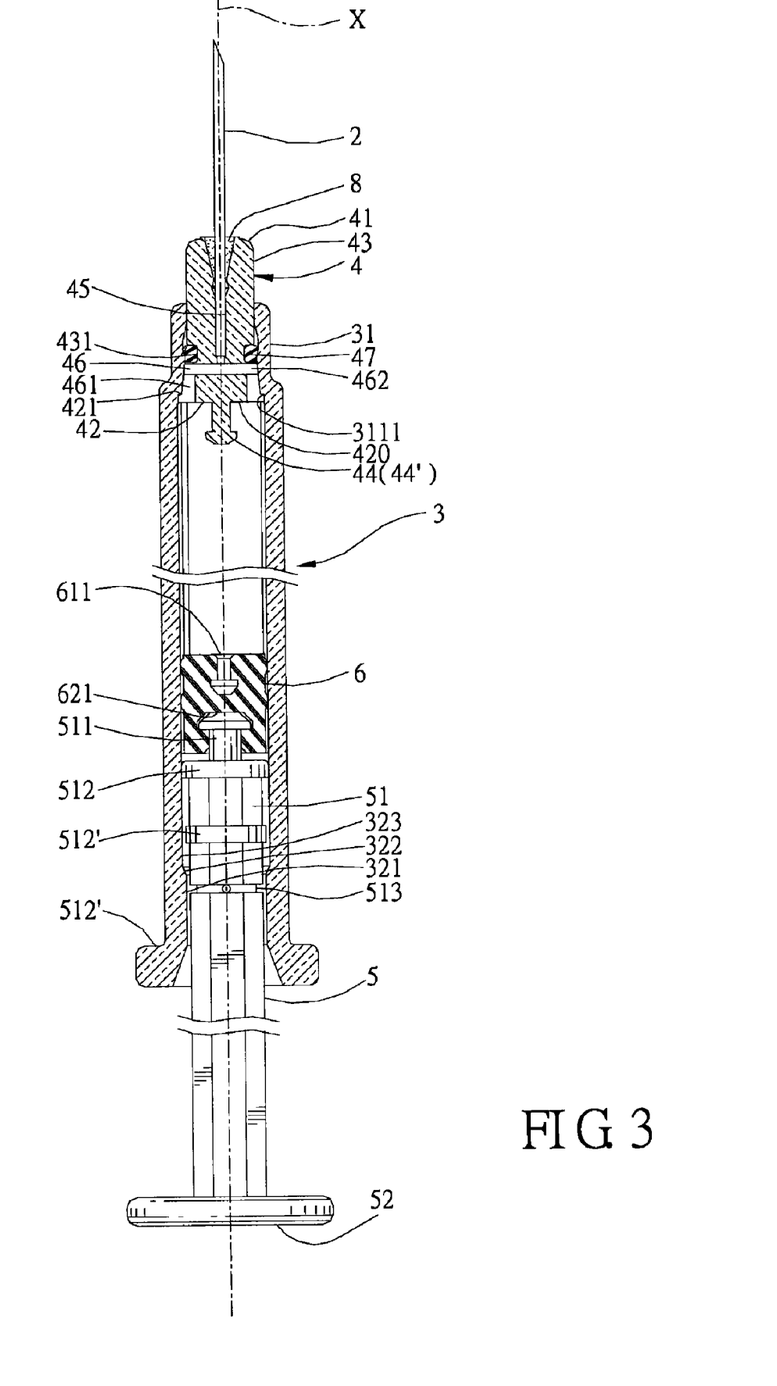
FIG. 3 is a fragmentary, partly sectional view of the first preferred embodiment.
Figure 4:
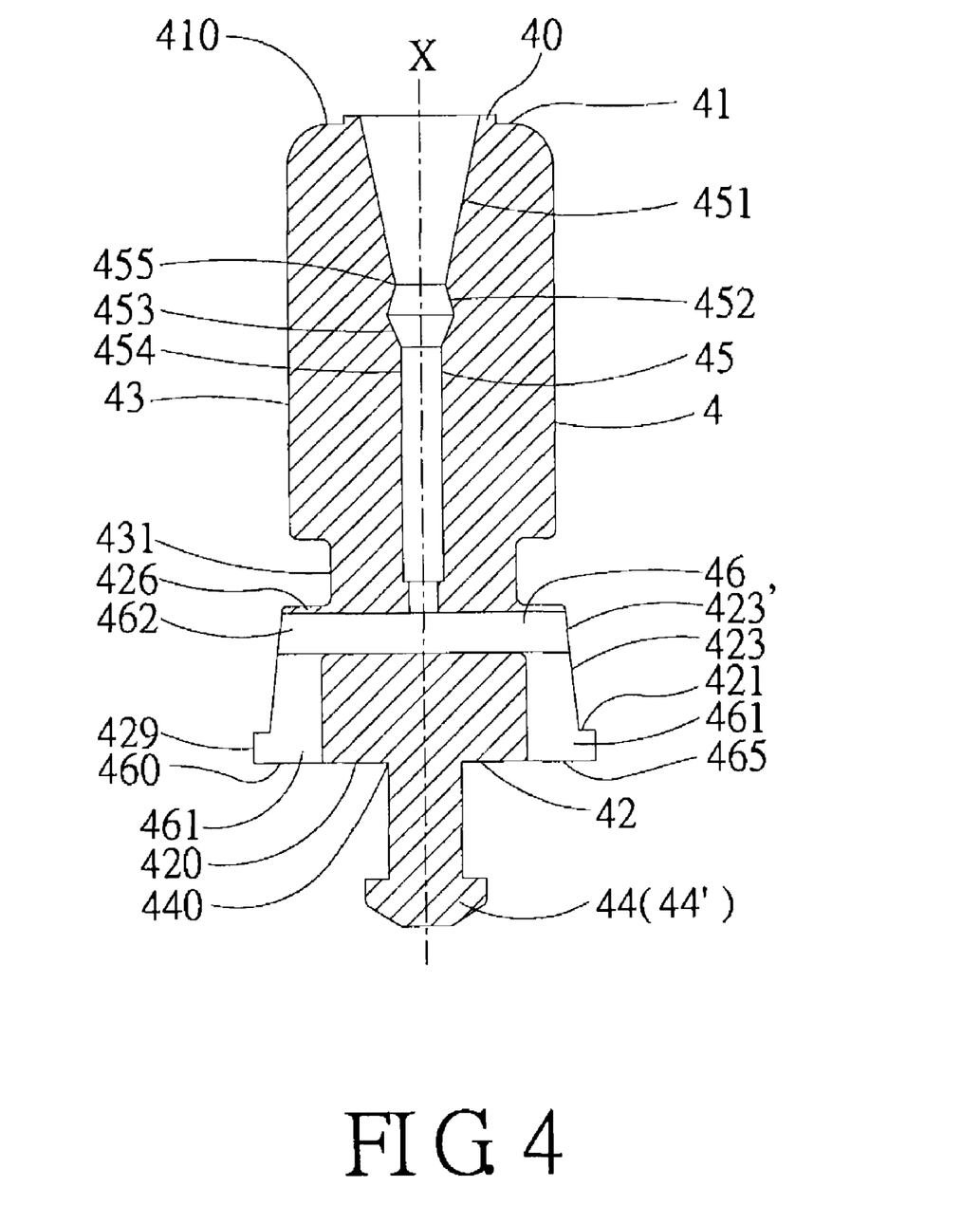
FIG. 4 is a sectional view of a needle seat of the first preferred embodiment.

Referring to FIGS. 2 to 4, the first preferred embodiment of a safety disposable syringe according to the present invention is shown to include: a barrel 3 having front and rear open ends 31, 32 and defining a chamber 30 therein and an axis (X); a plunger 5 extending through the rear open end 32 and into the chamber 30 and having a front end 51 formed with a protrusion 511; a piston 6 mounted on the front end 51 of the plunger 5 and formed with a rear recess 621 for extension of the protrusion 511 therein, and a first engaging member 611' opposite to the rear recess 621; a canula 2; and a needle seat 4 extending fittingly through the front open end 31 of the barrel 3 and having a front end 41 disposed outwardly of the chamber 30, and a rear end 42 disposed in the chamber 30 and having a rear end face 420 facing toward the piston 6. The needle seat 4 defines a central channel 45 extending through the front end 41 of the needle seat 4 for extension of the canula 2 thereinto, and a fluid passage 46 extending through the rear end face 420 of the rear end 42 of the needle seat 4 and in fluid communication with the central channel 45 and the chamber 30. The rear end face 420 of the rear end 42 of the needle seat 4 is formed with a second engaging member 44' that is axially aligned and that is engagable with the first engaging member 611' (see FIG. 6). The fluid passage 46 has a first terminating end 460 (see FIG. 4) terminated at the rear end face 420 of the rear end 42 of the needle seat 4. The second engaging member 44' has a terminating end 440 (see FIG. 4) terminated at the rear end face 420 of the rear end 42 of the needle seat 4 and spaced apart from the first terminating end 460 of the fluid passage 46.

Preferably, the first and second engaging members 611', 44' are engageable with each other in a tongue-and-groove engaging manner. In this embodiment, the piston 6 is formed with an engaging groove 611 that defines the first engaging member 611', and the rear end face 420 of the rear end 42 of the needle seat 4 is formed with an engaging tongue 44 that defines the second engaging member 44'.

In this embodiment, the needle seat 4 is in the form of a single piece. The engaging tongue 44 extends along the axis (X) of the barrel 3. The fluid passage 46 further has a second terminating end 465 (see FIG. 4) opposite to the first terminating end 460 and terminated at the rear end face 420 of the rear end 42 of the needle seat 4. The first and second terminating ends 460, 465 of the fluid passage 46 are disposed at two sides of the engaging tongue 44. The rear end 42 of the needle seat 4 has a peripheral edge 423. In this embodiment, the fluid passage 46 is generally U-shaped and has a radially extending section 462 extending through the peripheral edge 423 of the rear end 42 of the needle seat 4, and two axially extending sections 461 extending axially and respectively from two ends of the radially extending section 462 to the first and second terminating ends 460, 465.

The front end 41 of the needle seat 4 has a front end face 410. The central channel 45 has a first section 451 extending from the front end face 410 of the front end 41 of the needle seat 4, a second section 452 extending from the first section 451, a third section 453 extending from the second section 452, and a fourth section 454 extending from the third section 453 to the fluid passage 46. The first section 451 converges in dimensions from the front end face 410 of the front end 41 of the needle seat 4 to an adjacent end of the second section 452. The second section 452 diverge in dimensions from an adjacent end of the first section 451 to an adjacent end of the third section 453 so as to form a constriction 455 between the first and second sections 451, 452 for constricting the canula 2. A glue 8 fills the first section 451 of the central channel 45 to fix the canula 2 to the needle seat 4. The rear end 42 of the needle seat 4 is formed with a neck 421. The barrel 3 is formed with an inner shoulder 3111 disposed adjacent to the front open end 31 of the barrel 3 and abutting against the neck 421 of the rear end 42 of the needle seat 4 so as to prevent undesired removal of the needle seat 4 through the front open end 31 of the barrel 3.

The needle seat 4 has a tubular wall 40 (see FIGS. 2 and 4) that defines the central channel 45 therein, a plurality of angularly displaced fins 43 radiating from an outer surface of the tubular wall 40 and in frictional contact with an inner surface of the front open end 31 of the barrel 3, and an annular flange 471 connected to ends of the fins 43. The needle seat 4 is formed with an annular retaining groove 431 between the annular flange 471 and the radially extending section 462 of the fluid passage 46. A sealing ring 47 is retained in the retaining groove 431, and is in sealing contact with the inner surface of the front open end 31 of the barrel 3.

The barrel 3 has a rear end portion having an inner surface that has a cylindrical rear segment 321 extending from the rear open end 32 of the barrel 3, a middle segment 323, and a transition segment 322 interconnecting the rear segment 321 and the middle segment 323 and diverging in cross-section from the rear segment 321 to the middle segment 323. The plunger 5 further has a rear end 52, and is formed with an annular notch 513 disposed between the front and rear ends 51, 52 of the plunger 5, a first annular flange 512 axially spaced apart from the annular notch 513, and a second annular flange 512' disposed between the annular notch 513 and the first annular flange 512. The annular notch 513 is disposed between the second annular flange 512' and the rear end 52 of the plunger 5. The second annular flange 512' has a diameter substantially equal to that of the rear segment 321 of the barrel 3. The first annular flange 512 has a diameter substantially equal to that of the transition segment 322 of the barrel 3.

Figure 5:
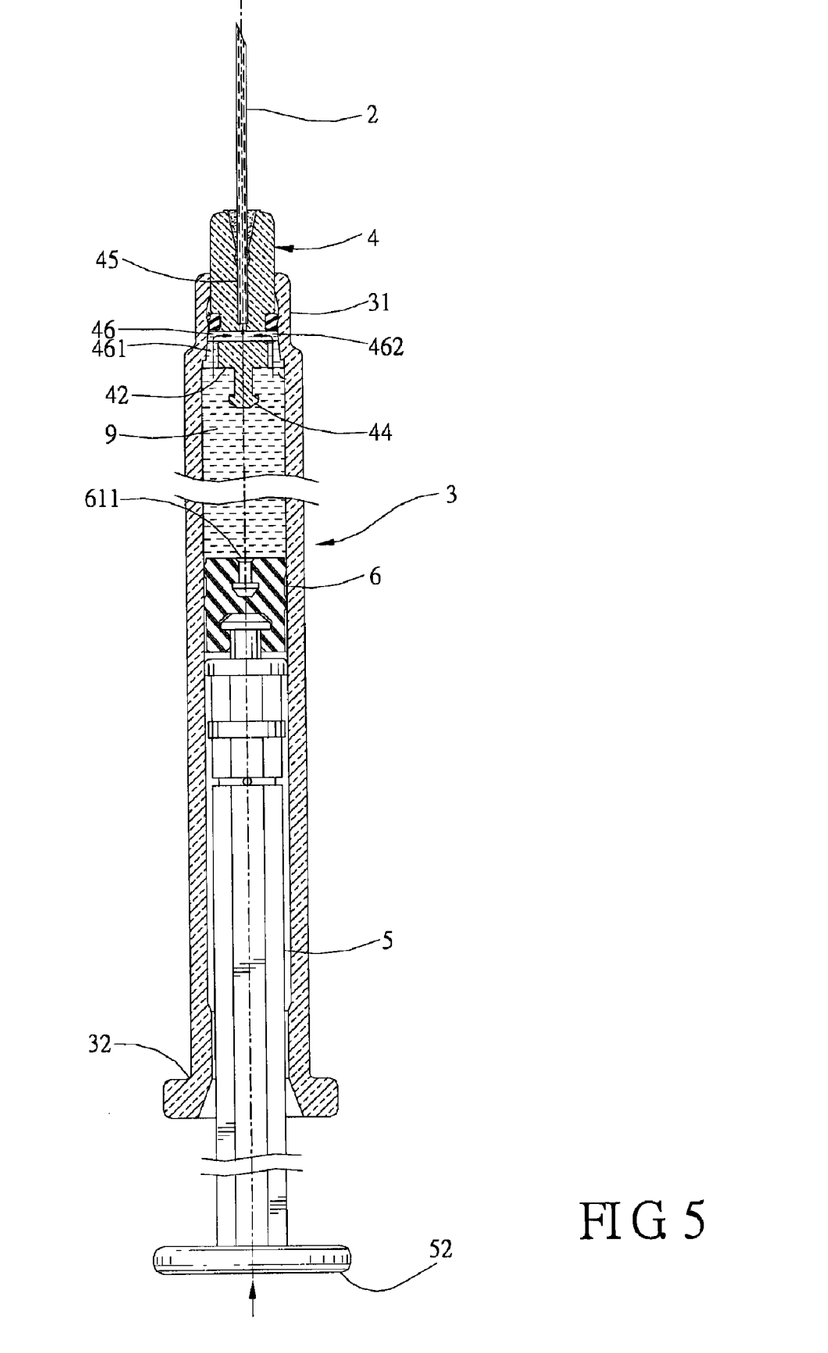
FIG. 5 is a fragmentary, partly sectional view illustrating how a fluid in a barrel is delivered through a fluid passage and a canula of the first preferred embodiment.
Figure 6:
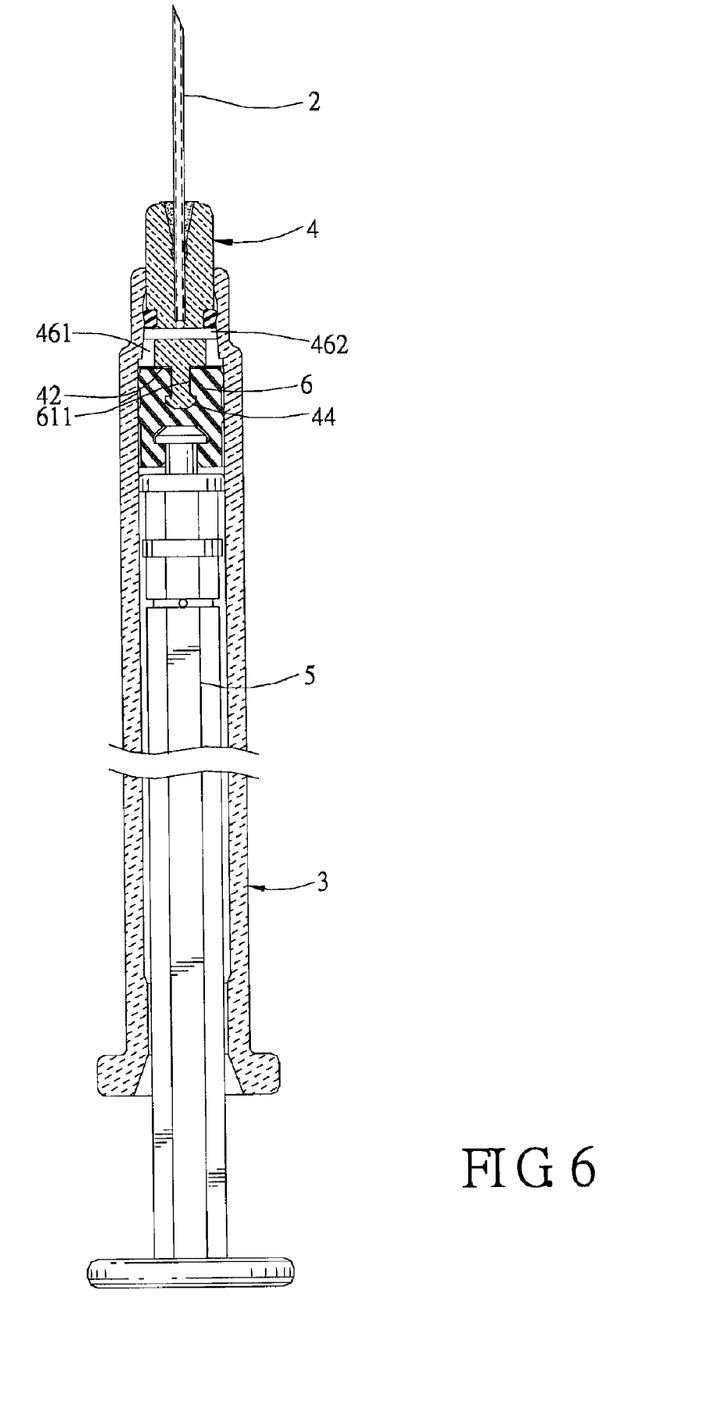
FIG. 6 is a fragmentary, partly sectional view illustrating how a piston is brought into engagement with the needle seat of the first preferred embodiment.
Figure 7:
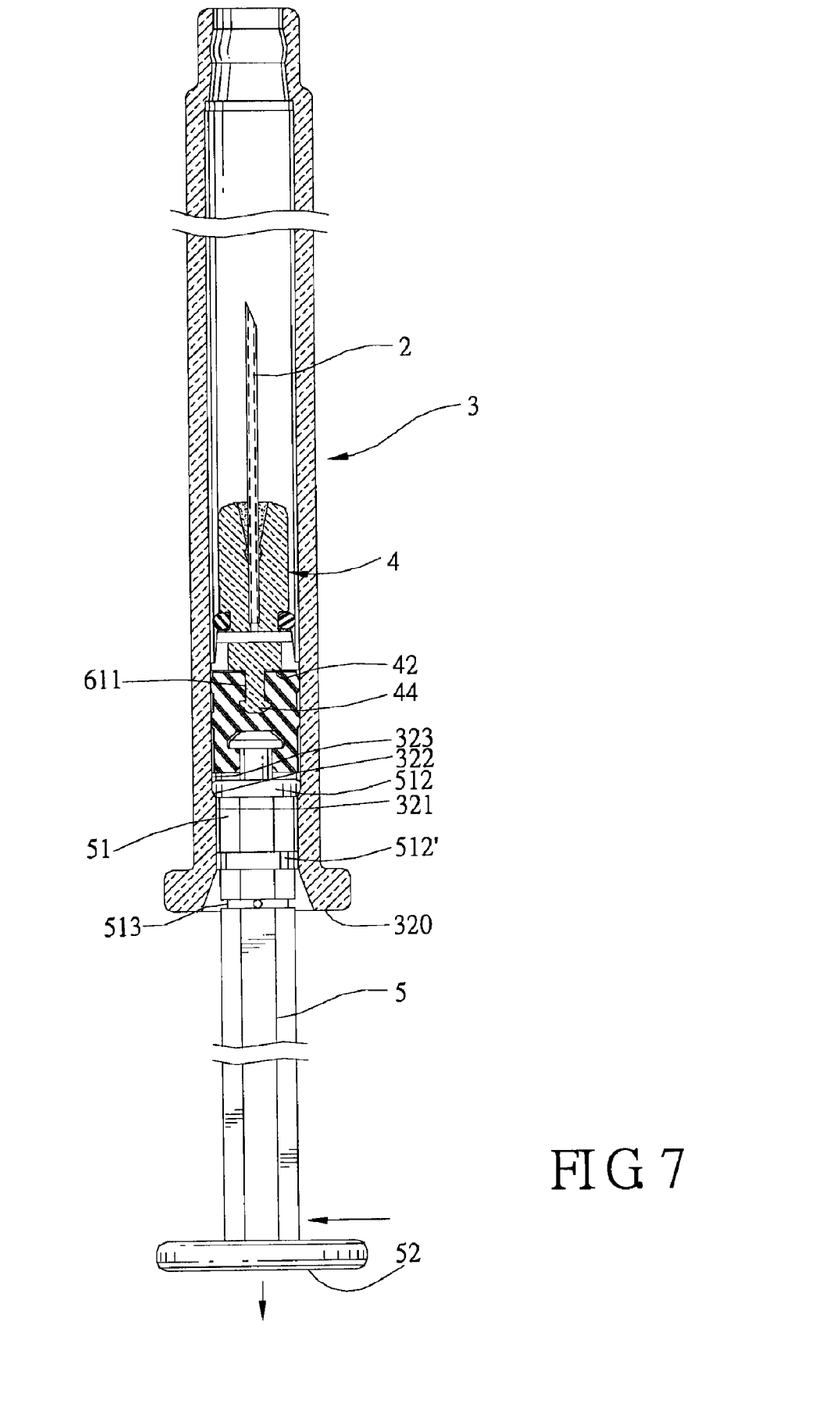
FIG. 7 is a fragmentary, partly sectional view illustrating how the needle seat together with the canula is withdrawn into the barrel of the first preferred embodiment.
Figure 8:
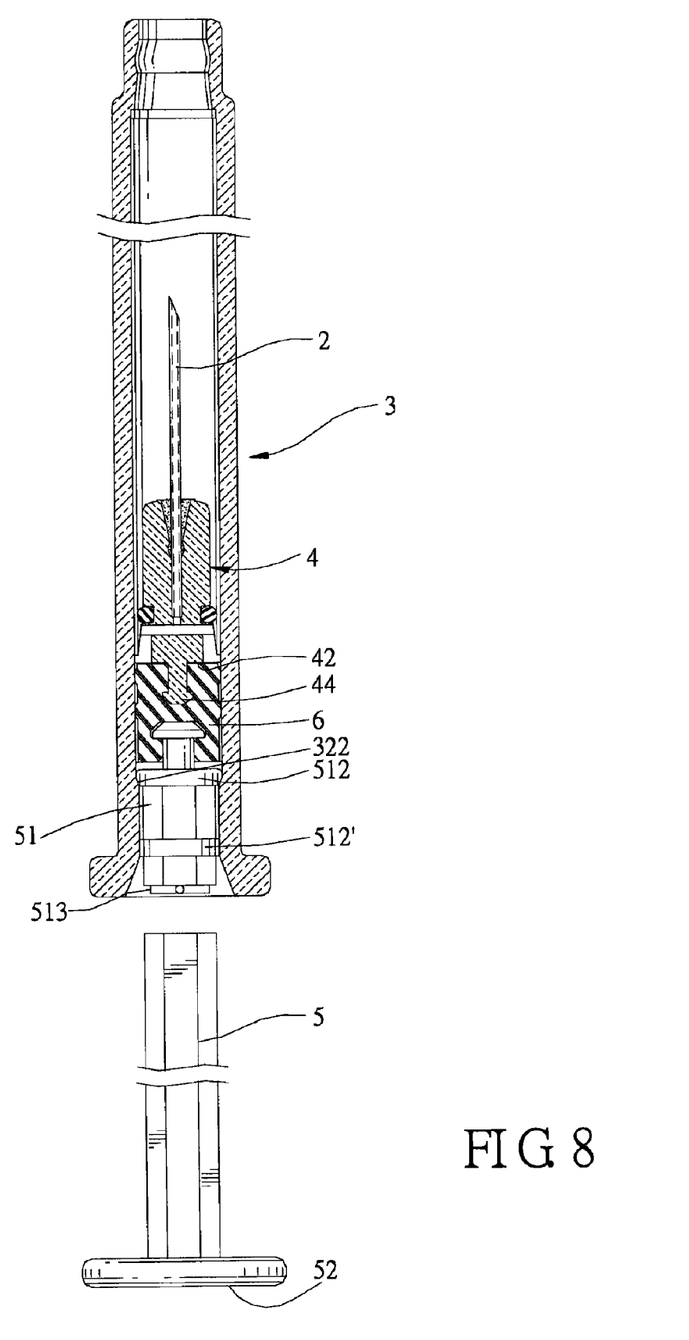
FIG. 8 is a fragmentary, partly sectional view illustrating how a portion of a plunger is removed after the needle is withdrawn into the barrel of the first preferred embodiment.

Referring to FIGS. 5 to 7, in operation, a fluid 9 in the barrel 3 is pushed by an external force acting on the plunger 5, and passes through the fluid passage 46 and the canula 2 for injection into a patient, When the engaging groove 611 in the piston 6 is brought into full engagement with the engaging tongue 44, the fluid 9 in the barrel 3 is completely expelled therefrom, as best illustrated in FIG. 6. When the safety disposable syringe is to be discarded after use, the plunger 5 is pulled back so as to withdraw the needle seat 4 together with the canula 2 in to the barrel 3, as best illustrated in FIG. 7. When the first annular flange 512 of the plunger 5 is brought into abutment against the transition segment 322 of the inner surface of the rear end portion of the barrel 3, further rearward movement of the plunger 5 is prevented. At this state, the annular notch 513 is substantially blush with a rear end face 420 of the barrel 3, thereby permitting breaking of the plunger 5 at the annular notch 513 (see FIG. 8).

Figure 9:
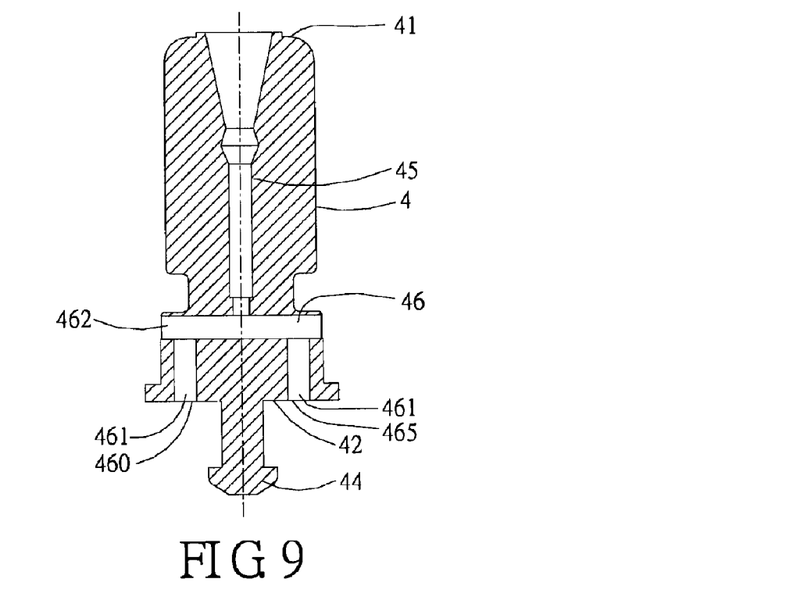
FIG. 9 is a sectional view of the needle seat of the second preferred embodiment of the safety disposable syringe according to this invention.

FIG. 9 illustrates the second preferred embodiment of the safety disposable syringe according to this invention. The second preferred embodiment differs from the previous embodiment in that the axially extending sections 461 of the fluid passage 46 extend axially from the radially extending section 462 at positions between the two ends of the radially extending section 462.

Figure 10:
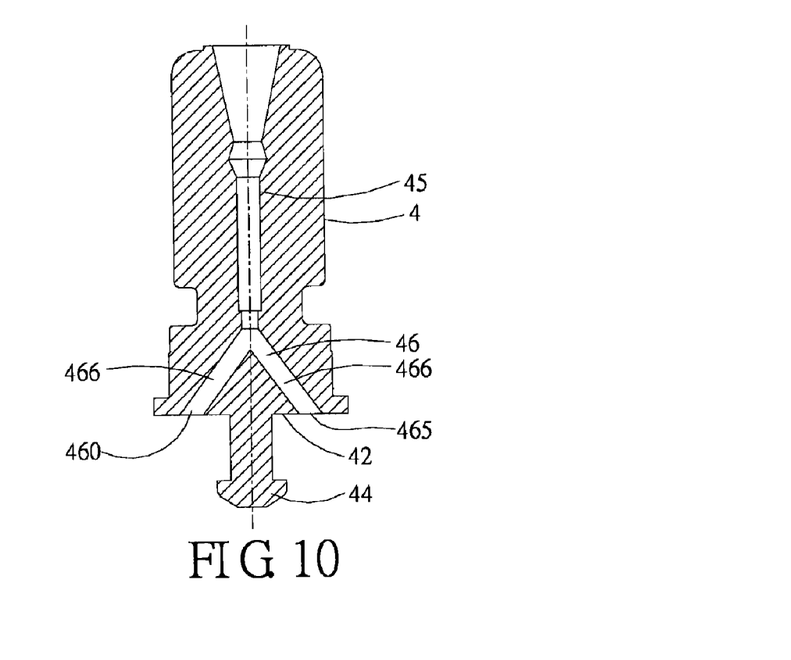
FIG. 10 is a sectional view of the needle seat of the third preferred embodiment of the safety disposable syringe according to this invention.

FIG. 10 illustrates the third preferred embodiment of the safety disposable syringe according to this invention. The third preferred embodiment differs from the previous embodiments in that the fluid passage 46 is generally V-shaped, and includes two sections 466 merging at an adjacent end of the central channel 45 and inclined relative to the axis (X).

Figure 11:
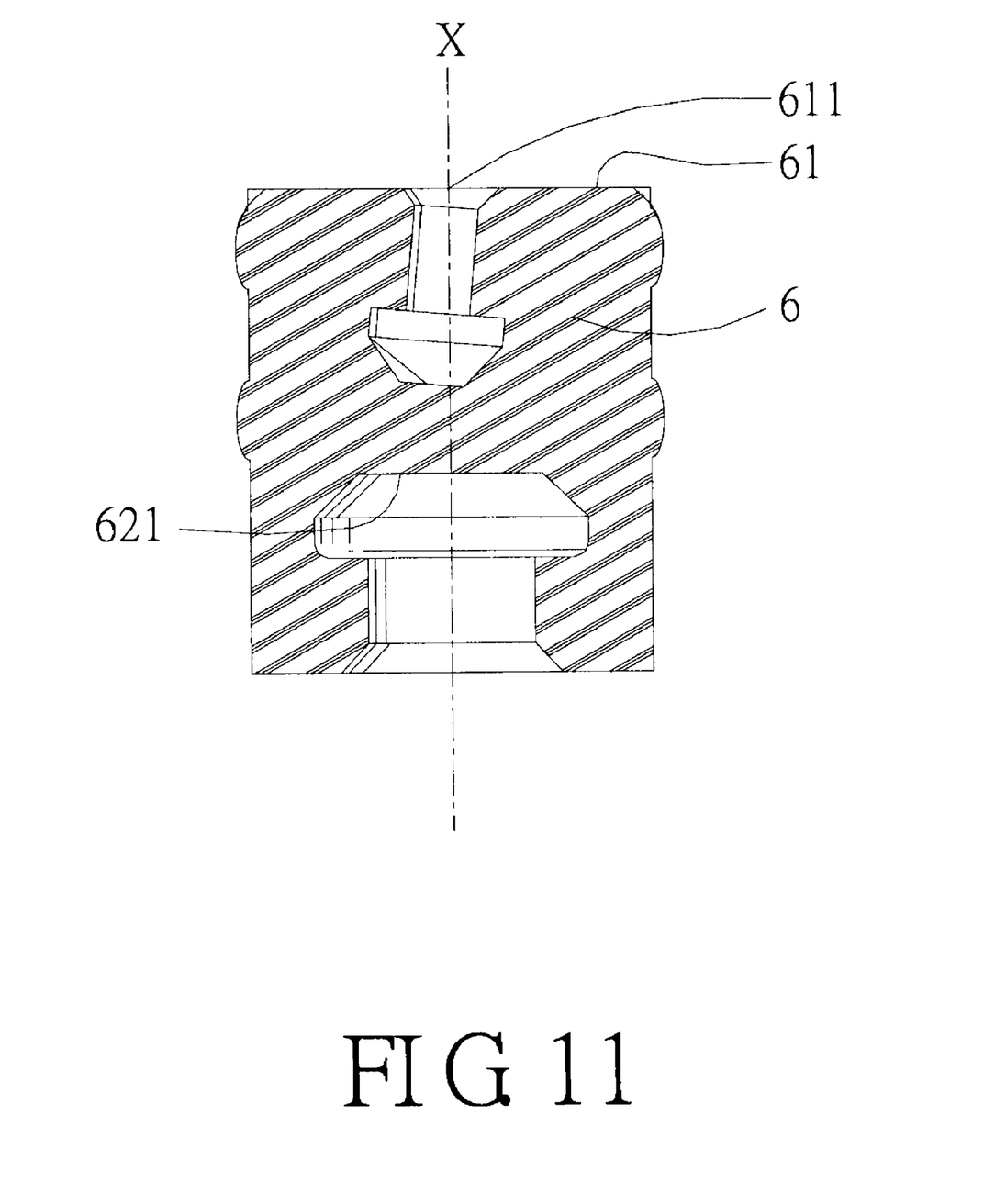
FIG. 11 is a sectional view of a piston of the fourth preferred embodiment of the safety disposable syringe according to this invention.
Figure 12:
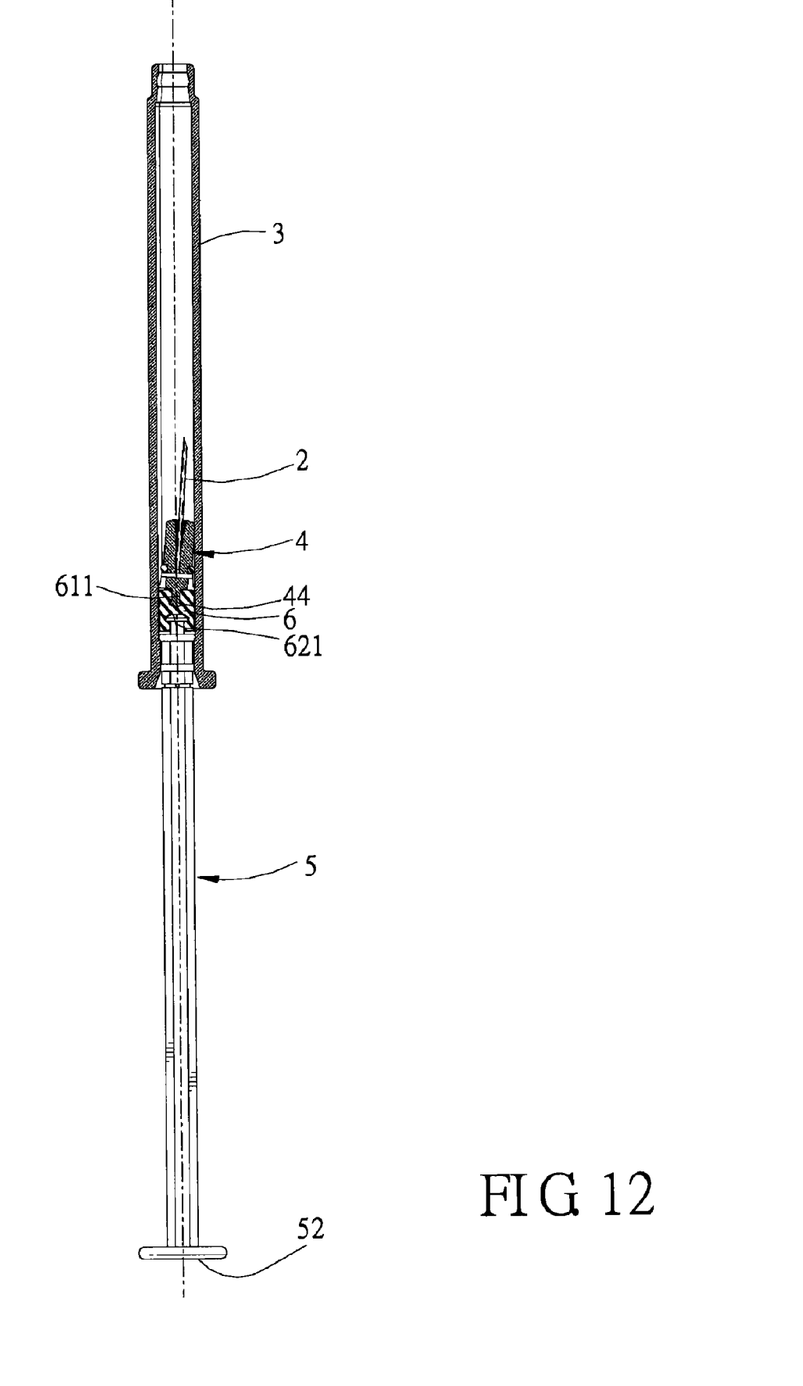
FIG. 12 is a partly sectional view illustrating a state where the needle seat together with the canula tilts at an angle relative to an axis after being withdrawn into the barrel of the fourth preferred embodiment.

FIGS. 11 and 12 illustrate the fourth preferred embodiment of the safety disposable syringe according to this invention. The fourth preferred embodiment differs from the previous embodiments in that the engaging groove 611 in the piston 6 is tilted relative to the axis (X) of the barrel 3 so as to permit tilting of the needle seat 4 together with the canula 2 relative to the axis (X) when the needle seat 4 and the canula 2 are withdrawn into the barrel 3.

Figure 13:
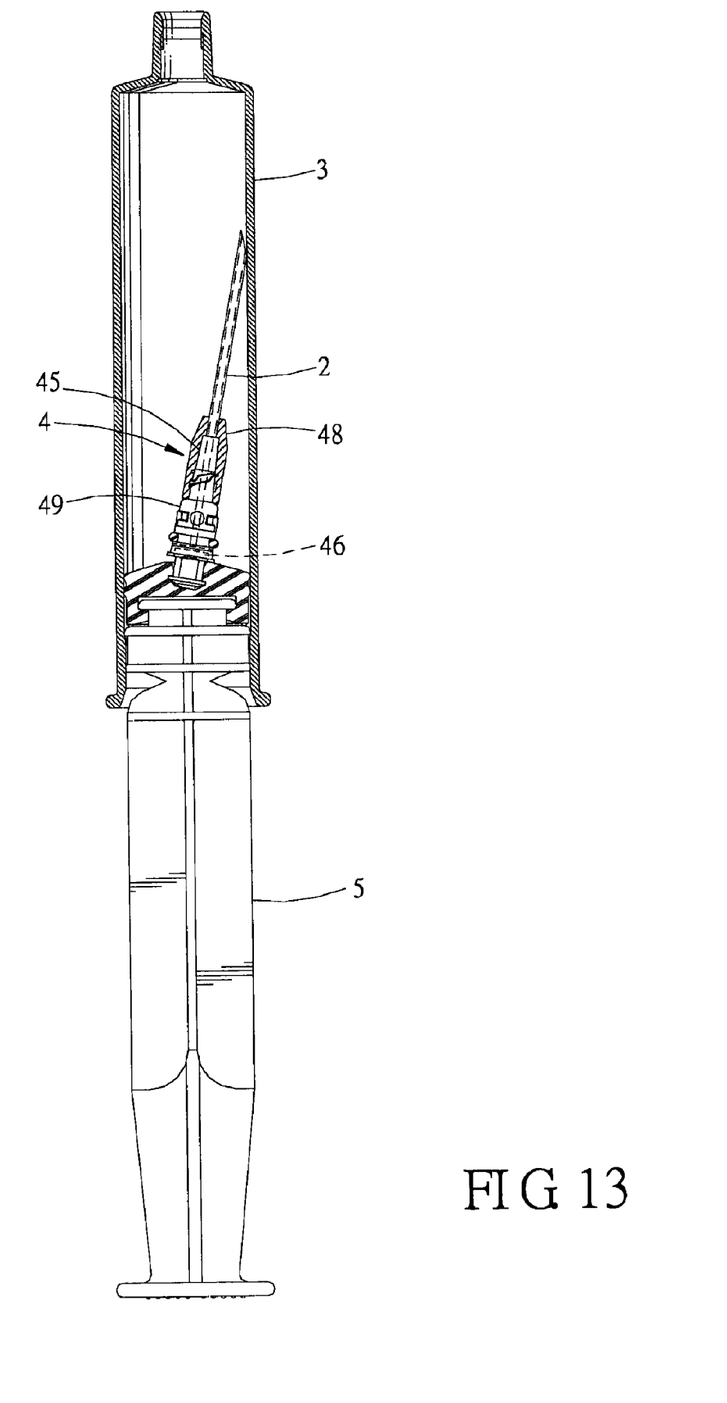
FIG. 13 is a partly sectional view illustrating a state where the needle seat together with the canula tilts at an angle relative to the axis after being withdrawn into the barrel of the fifth preferred embodiment of the safety disposable syringe according to this invention.

FIG. 13 illustrates the fifth preferred embodiment of the safety disposable syringe according to this invention. The fifth preferred embodiment differs from the previous embodiments in that the needle seat 4 includes first and second pieces 48, 49 which are threadedly engaged. The canula 2 is inserted into the central channel 45 in the first piece 48. The fluid passage 46 is formed in the second piece 49.

As illustrated in the preferred embodiments, by forming the fluid passage 46 in the needle seat 4 such that it does not pass through the second engaging member 44' (i.e., the engaging protrusion 44 formed on the rear end face 420 of the rear end 42 of the needle seat 4), the size of the second engaging member 44' can be kept as small as possible as long as engagement between the first and second engaging members 611', 44' is sufficient to permit withdrawal of the needle seat 4 into the barrel 3 by the plunger 5, thereby eliminating the aforesaid drawback associated with the prior art.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

What is claimed is:

1. A safety disposable syringe comprising:
   (a) a barrel comprising front and rear open ends and defining a chamber therein and an axis, said barrel being formed with an inner shoulder adjacent to said front open end;
   (b) a plunger extending through said rear open end and into said chamber, and comprising a front end;
   (c) a piston mounted on said front end of said plunger and formed with a first engaging member;
   (d) a cannula;
   (e) a needle seat extending fittingly through said front open end of said barrel and comprising
      (i) a front seat portion that has a front end disposed outwardly of said chamber, and that defines a central channel extending through said front end of said front seat portion for extension of said cannula thereinto, and
      (ii) a rear seat portion that is disposed in said chamber, and that extends away from said front seat portion to terminate at a rear surface confronting said piston, said rear seat portion having an outer surface that surrounds the axis and that is in frictional contact with an inner surface of said front open end of said barrel, said outer surface defining an annular retaining groove that is disposed proximate to said front seat portion;
   (f) an engaging flange extending radially and outwardly from said rear surface, and configured to abut against said inner shoulder of said barrel axially;
   wherein said rear seat portion defines a fluid passage comprising:
      (i) a radially extending section that communicates with said central channel, and that extends outwardly through said outer surface so as to communicate with said inner surface of said front open end of said barrel, said radially extending section being disposed below and separated from said annular retaining groove by a partition region that borders said radially extending section, and
      (ii) at least one axially extending section that is formed in said rear surface adjacent to said engaging flange, that extends axially towards said front seat portion and along said outer surface to communicate with said radially extending section, and that terminates at said partition region;
   (g) a second engaging member disposed on said rear surface, and axially aligned and engageable with said first engaging member; and
   (h) a sealing ring retained in said retaining groove and in sealing contact with said inner surface of said front open end of said barrel,
   wherein said radially extending section of said fluid passage has opposite ends, which are at the opposite sides of said central channel, and which extend outwardly through said outer surface of said rear seat portion of said needle seat respectively, said fluid passage having a pair of axially extending sections extending axially towards said front seat portion of said needle seat along said outer surface to communicate respectively with said opposite ends of said radially extending section and terminating at said partition region.

2. A safety disposable syringe comprising:
   (a) a barrel comprising front and rear open ends and defining a chamber therein and an axis, said barrel being formed with an inner shoulder adjacent to said front open end;
   (b) a plunger extending through said rear open end and into said chamber, and comprising a front end;
   (c) a piston mounted on said front end of said plunger and formed with a first engaging member;
   (d) a cannula;
   (e) a needle seat extending fittingly through said front open end of said barrel and comprising
      (i) a front seat portion that has a front end disposed outwardly of said chamber, and that defines a central channel extending through said front end of said front seat portion for extension of said cannula thereinto, and
      (ii) a rear seat portion that is disposed in said chamber, and that extends away from said front seat portion to terminate at a rear surface confronting said piston, said rear seat portion having an outer surface that surrounds the axis and that is in frictional contact with an inner surface of said front open end of said barrel, said outer surface defining an annular retaining groove that is disposed proximate to said front seat portion;
   (f) an engaging flange extending radially and outwardly from said rear surface, and configured to abut against said inner shoulder of said barrel axially;
   wherein said rear seat portion defines a fluid passage comprising:
      (i) a radially extending section that communicates with said central channel, and that extends outwardly through said outer surface so as to communicate with said inner surface of said front open end of said barrel, said radially extending section being disposed below and separated from said annular retaining groove by a partition region that borders said radially extending section, and
      (ii) at least one axially extending section that is formed in said rear surface adjacent to said engaging flange, that extends axially towards said front seat portion and along said outer surface to communicate with said radially extending section, and that terminates at said partition region;
   (g) a second engaging member disposed on said rear surface, and axially aligned and engageable with said first engaging member; and
   (h) a sealing ring retained in said retaining groove and in sealing contact with said inner surface of said front open end of said barrel,
   wherein said front end of said front seat portion of said needle seat comprises a front surface, said central channel comprising a first section extending from said front surface, a second section extending from said first section, and a third section extending from said second section, said first section converging in dimensions from said front surface to an adjacent end of said second section, said second section diverging in dimensions from an adjacent end of said first section to an adjacent end of said third section so as to form a constriction between said first and second sections for constricting said cannula.

3. A safety disposable syringe comprising:
(a) a barrel comprising front and rear open ends and defining a chamber therein and an axis, said barrel being formed with an inner shoulder adjacent to said front open end;
(b) a plunger extending through said rear open end and into said chamber, and comprising a front end;
(c) a piston mounted on said front end of said plunger and formed with a first engaging member;
(d) a cannula;
(e) a needle seat extending fittingly through said front open end of said barrel and comprising
   (i) a front seat portion that has a front end disposed outwardly of said chamber, and that defines a central channel extending through said front end of said front seat portion for extension of said cannula thereinto, and
   (ii) a rear seat portion that is disposed in said chamber, and that extends away from said front seat portion to terminate at a rear surface confronting said piston, said rear seat portion having an outer surface that surrounds the axis and that is in frictional contact with an inner surface of said front open end of said barrel, said outer surface defining an annular retaining groove that is disposed proximate to said front seat portion;
(f) an engaging flange extending radially and outwardly from said rear surface, and configured to abut against said inner shoulder of said barrel axially;
wherein said rear seat portion defines a fluid passage comprising:
   (i) a radially extending section that communicates with said central channel, and that extends outwardly through said outer surface so as to communicate with said inner surface of said front open end of said barrel, said radially extending section being disposed below and separated from said annular retaining groove by a partition region that borders said radially extending section, and
   (ii) at least one axially extending section that is formed in said rear surface adjacent to said engaging flange, that extends axially towards said front seat portion and along said outer surface to communicate with said radially extending section, and that terminates at said partition region;
(g) a second engaging member disposed on said rear surface, and axially aligned and engageable with said first engaging member; and
(h) a sealing ring retained in said retaining groove and in sealing contact with said inner surface of said front open end of said barrel,
wherein said needle seat has a tubular wall that defines said central channel therein, and a plurality of angularly displaced fins radiating radially and outwardly from an outer surface of said tubular wall and in frictional contact with said inner surface of said front open end of said barrel.

4. A safety disposable syringe comprising:
(a) a barrel comprising:
   (i) front and rear open ends and defining a chamber therein and an axis, said barrel being formed with an inner shoulder adjacent to said front open end; and
   (ii) a rear end portion having an inner surface that has a cylindrical rear segment extending from said rear open end of said barrel, a middle segment, and a transition segment interconnecting said rear segment and said middle segment and diverging in cross-section from said rear segment to said middle segment;
(b) a plunger extending through said rear open end and into said chamber, and comprising:
   (i) a front end; and
   (ii) a rear end and is formed with an annular notch disposed between said front and rear ends of said plunger, a first annular flange axially spaced apart from said annular notch, and a second annular flange disposed between said annular notch and said first annular flange, said annular notch being disposed between said second annular flange and said rear end of said plunger, said second annular flange having a diameter substantially equal to that of said rear segment of said barrel, said first annular flange having a diameter substantially equal to that of said transition segment of said barrel
(c) a piston mounted on said front end of said plunger and formed with a first engaging member;
(d) a cannula;
(e) a needle seat extending fittingly through said front open end of said barrel and comprising
   (i) a front seat portion that has a front end disposed outwardly of said chamber, and that defines a central channel extending through said front end of said front seat portion for extension of said cannula thereinto, and
   (ii) a rear seat portion that is disposed in said chamber, and that extends away from said front seat portion to terminate at a rear surface confronting said piston, said rear seat portion having an outer surface that surrounds the axis and that is in frictional contact with an inner surface of said front open end of said barrel, said outer surface defining an annular retaining groove that is disposed proximate to said front seat portion;
(f) an engaging flange extending radially and outwardly from said rear surface, and configured to abut against said inner shoulder of said barrel axially;
wherein said rear seat portion defines a fluid passage comprising:
   (i) a radially extending section that communicates with said central channel, and that extends outwardly through said outer surface so as to communicate with said inner surface of said front open end of said barrel, said radially extending section being disposed below and separated from said annular retaining groove by a partition region that borders said radially extending section, and
   (ii) at least one axially extending section that is formed in said rear surface adjacent to said engaging flange, that extends axially towards said front seat portion and along said outer surface to communicate with said radially extending section, and that terminates at said partition region;
(g) a second engaging member disposed on said rear surface, and axially aligned and engageable with said first engaging member; and
(h) a sealing ring retained in said retaining groove and in sealing contact with said inner surface of said front open end of said barrel.

5. A safety disposable syringe comprising:
(a) a barrel comprising front and rear open ends and defining a chamber therein and an axis, said barrel being formed with an inner shoulder adjacent to said front open end;

(b) a plunger extending through said rear open end and into said chamber, and comprising a front end;
(c) a piston mounted on said front end of said plunger and formed with a first engaging member;
(d) a cannula;
(e) a needle seat extending fittingly through said front open end of said barrel and comprising
   (i) a front seat portion that has a front end disposed outwardly of said chamber, and that defines a central channel extending through said front end of said front seat portion for extension of said cannula thereinto, and
   (ii) a rear seat portion that is disposed in said chamber, and that extends away from said front seat portion to terminate at a rear surface confronting said piston, said rear seat portion having an outer surface that surrounds the axis and that is in frictional contact with an inner surface of said front open end of said barrel, said outer surface defining an annular retaining groove that is disposed proximate to said front seat portion;
(f) an engaging flange extending radially and outwardly from said rear surface, and configured to abut against said inner shoulder of said barrel axially;
wherein said rear seat portion defines a fluid passage comprising:
   (i) a radially extending section that communicates with said central channel, and that extends outwardly through said outer surface so as to communicate with said inner surface of said front open end of said barrel, said radially extending section being disposed below and separated from said annular retaining groove by a partition region that borders said radially extending section, and
   (ii) at least one axially extending section that is formed in said rear surface adjacent to said engaging flange, that extends axially towards said front seat portion and along said outer surface to communicate with said radially extending section, and that terminates at said partition region;
(g) a second engaging member disposed on said rear surface, and axially aligned and engageable with said first engaging member; and
(h) a sealing ring retained in said retaining groove and in sealing contact with said inner surface of said front open end of said barrel, and
wherein said first and second engaging members are engageable with each other in a tongue-and-groove engaging manner,
wherein said piston is formed with an engaging groove that serves as said first engaging member, said second engaging member being configured to be an engaging tongue, and
wherein said engaging groove in said piston is tilted relative to the axis of said barrel.

* * * * *